United States Patent [19]
Enenkel

[11] Patent Number: 4,773,315
[45] Date of Patent: Sep. 27, 1988

[54] CONTROL ARRANGEMENT FOR A VINEGAR FERMENTATION PROCESS

[75] Inventor: Anton Enenkel, Bonn, Fed. Rep. of Germany

[73] Assignee: Heinrich Frings GmbH & Co. KG, Bonn, Fed. Rep. of Germany

[21] Appl. No.: 120,490

[22] Filed: Nov. 13, 1987

[30] Foreign Application Priority Data

Nov. 13, 1986 [AT] Austria .................. 3018/86

[51] Int. Cl.$^4$ .................. C12J 1/04; 426 8; 426 17; 426 15; 426 118
[52] U.S. Cl. .................. 99/323.12; 99/277
[58] Field of Search ............ 99/323.12, 323.1, 277.1, 99/275–278, 486, 516; 426/8, 17, 15, 118; 435/140, 291, 311, 313, 315, 316, 289

[56] References Cited

U.S. PATENT DOCUMENTS

| | | | |
|---|---|---|---|
| 2,236,153 | 3/1941 | Owens | 99/323.12 |
| 2,390,717 | 12/1945 | Knebel | 99/323.12 |
| 4,076,844 | 2/1978 | Ebner et al. | 426/17 |
| 4,264,740 | 4/1981 | Christ et al. | 99/277.2 |
| 4,593,611 | 6/1986 | Bruch | 99/277.1 |
| 4,711,163 | 12/1987 | Capuano | 99/323.12 |

FOREIGN PATENT DOCUMENTS

| | | |
|---|---|---|
| 237560 | 5/1964 | Austria . |
| 264429 | 12/1967 | Austria . |
| 363053 | 2/1979 | Austria . |
| 3514634 | 11/1985 | Fed. Rep. of Germany . |
| 1305868 | 2/1973 | United Kingdom . |

Primary Examiner—Timothy F. Simone
Attorney, Agent, or Firm—Norbert P. Holler

[57] ABSTRACT

A control arrangement for a two-stage submerged vinegar fermentation process for producing vinegar with a high acetic acid concentration of more than 15% is disclosed. The fermentation system includes a main fermentation tank and a secondary fermentation tank, a connecting line with a shut-off valve and a feed pump incorporated therein extending between the two tanks, separate mash and alcohol feed lines with incorporated feed pumps connected to the main fermentation tank, and a vinegar discharge feed line with an incorporated feed pump connected to the secondary fermentation tank. The control arrangement includes an alcohol analyzer and a liquid level sensing device on each of the tanks, a volume flowmeter incorporated in the alcohol feed line, and a controller for each of the tanks. The control connections are such that alcohol is charged into the main fermentation tank in dependence on the alcohol concentration therein, substrate is discharged into the secondary fermentation tank from the main fermentation tank in dependence on the quantity of alcohol charged into the latter, with the transfer being terminated when the liquid in the main fermentation tank reaches a preset lower level, and vinegar is discharged from the secondary fermentation tank in dependence on the alcohol concentration therein having decreased to a predetermined minimum, with the connecting line between the tanks being blocked until the liquid in the secondary fermentation tank has fallen to a preset lowest level.

7 Claims, 1 Drawing Sheet

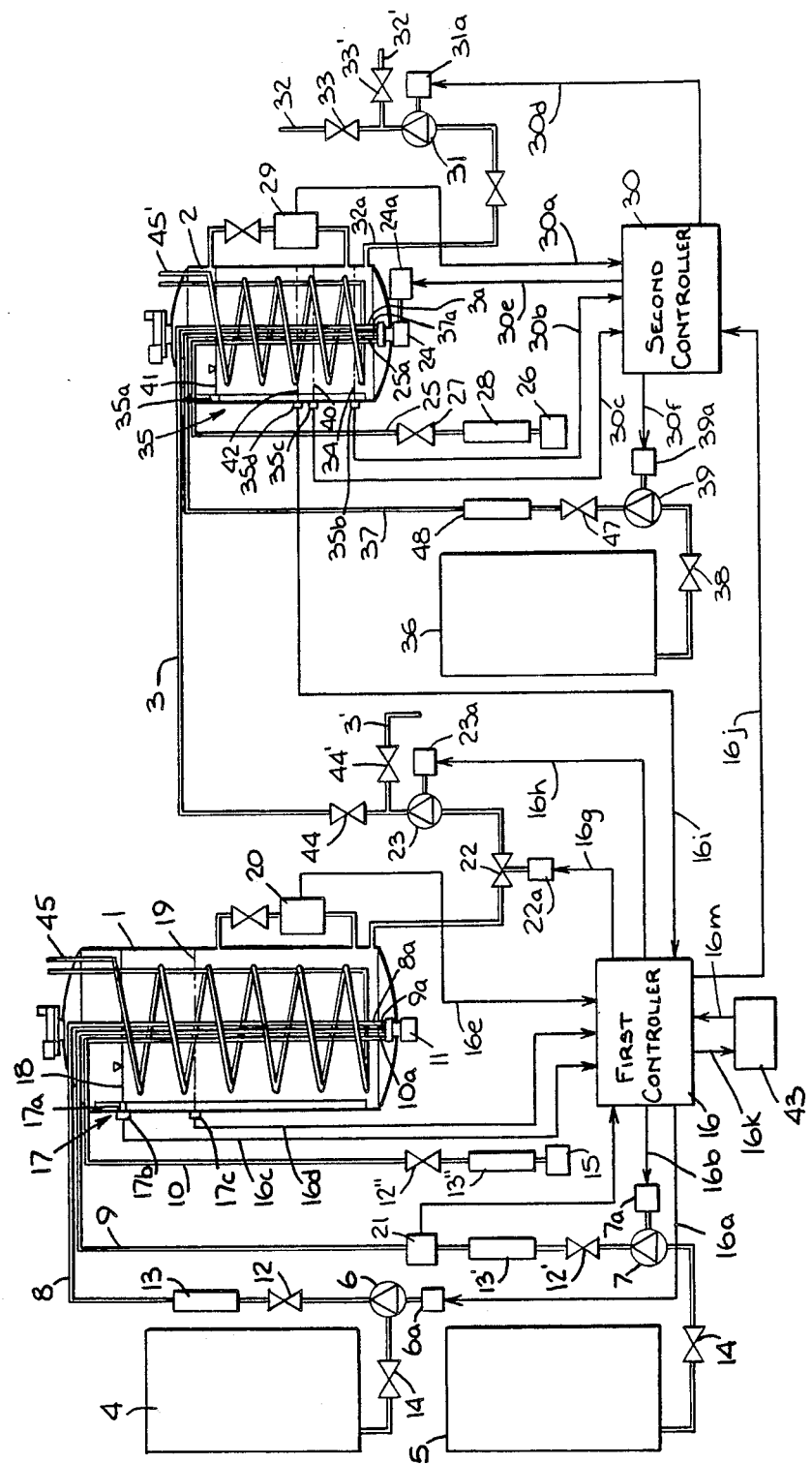

CONTROL ARRANGEMENT FOR A VINEGAR FERMENTATION PROCESS

This invention relates to an arrangement for controlling a vinegar fermentation process, and in particular for controlling a two-stage submerged fermentation process for producing vinegar with a high acetic acid concentration of more than 15%, which process is carried out in a system including as known components a main fermentation tank, associated supply tanks for alcohol and mash connected to the main fermentation tank via respective feed lines each incorporating a respective feed pump, and at least one secondary fermentation tank connected with the main fermentation tank through a valved connecting line, with a respective aeration device being provided in each of the fermentation tanks, and a control device for activating the alcohol feed pump in dependence on the difference between the actual alcohol concentration of the liquid in the main fermentation tank (as determined by an analyzer) and a predetermined desired value for the alcohol concentration limit.

BACKGROUND OF THE INVENTION

A known two-stage submerged vinegar fermentation process and the associated equipment for producing vinegar with an acetic acid concentration of more than 15 g/100 ml are described in Austrian Pat. No. 363,053. A description of that same process, but without a description of the equipment details, is also found in U.S. Pat. No. 4,076,844. In that process, during a first fermentation stage the total concentration (the sum of the alcohol and acetic acid concentrations, with alcohol concentration expressed in volume by volume and acetic acid concentration expressed in weight by volume) of the liquid in a main fermentation tank is increased to more than 15% from a starting value in the range of 12–15% at an alcohol content of from 1–5 vol. % by means of a slow addition of alcohol and in particular while the acetic acid concentration is limited to at most 15 g/100 ml. Thereafter, a part of the substrate is discharged from the main fermentation tank into a secondary fermentation tank in order to continue the fermentation, while the total concentration is kept constant, until the alcohol concentration has decreased to less than 0.5 vol. %.

This process is based on the recognition that the vinegar bacteria (Acetobacter), even after having lost the capacity for multiplication, are still capable, for a limited period of time, to support acidification, i.e., to oxidize alcohol into vinegar. In the known process, this capability, which depends on the existence of certain conditions, is put to use in the secondary fermentation tank, while in the main fermentation tank the multiplication capacity of the vinegar bacteria, which is required for the continuation of the fermentation, is maintained through a limiting of the acetic acid concentration. The quantity of substrate discharged from the main fermentation tank into the secondary fermentation tank is replaced through an injection of fresh mash into the main tank, by means of which the original starting concentrations of acetic acid and alcohol are again attained. As a consequence, in the main fermentation tank the fermentation can be repeated under conditions which are the same as before and until, through the gradual influx of alcohol to the extent of the alcohol oxidation, the total concentration of the substrate is again increased to above 15 % while the acetic acid concentration is concurrently limited to remain below 15 g/100 ml. At that point in time, a portion of the substrate in the main fermentation tank is again discharged therefrom and transferred into the secondary fermentation tank, after which the above-described fermentation proceeds anew.

As will be apparent from the description of the known process in the aforesaid Austrian patent, in that process the feed of alcohol into the main fermentation tank is controlled by a device which analyzes the alcohol concentration in the main tank, during which analysis the alcohol concentration as measured is compared with a predetermined desired value thereof. If the alcohol concentration sinks below the predetermined desired value, then the feed pump for the alcohol is activated until the desired value is again reached. Despite this control of the alcohol feed pump in dependence on the alcohol concentration in the main fermentation tank, the effort expended to assure an undisturbed running of the process is relatively great, because the acetic acid concentration in the main fermentation tank must be limited and care must be taken to achieve a properly timed transfer of a portion of the substrate from the main fermentation tank into the secondary fermentation tank. Thus, automatic monitoring and control is needed for the entire process.

A known single-stage fermentation process for producing vinegar with an acetic acid concentration of above 15 g/100 ml in a fermentation tank is described in German published patent application No. 3,514,634. In that process, the addition of alcohol to a mash having predetermined starting concentrations of acetic acid and alcohol is controlled in dependence on the instantaneous extent of the oxidation of the alcohol to vinegar. To this end, the acetic acid concentration on the one hand and the alcohol concentration on the other hand are periodically measured, and from the change of the acetic acid concentration per unit of time the amount of alcohol to be added over each unit of time, under the assumption of a constant increase in the acetic acid concentration up to a predetermined end concentration, is determined in a computer. With the help of the computer, the calculated desired value of the alcohol feed rate is compared with the measured actual value of the added quantity of alcohol in order to match the added quantity of alcohol to the desired value of the alcohol concentration through a balancing of the desired and actual values thereof. Apart from the fact that such a control of a single-stage fermentation process is not suited for use in a two-stage fermentation process, it suffers from the disadvantage that by virtue of the continuous matching of the added quantity of alcohol to the measurement of the instantaneous increase of the acetic acid concentration a continuous variation in the alcohol concentration is obtained, which adversely affects the vinegar fermentation.

SUMMARY OF THE INVENTION

The basic objective of the present invention is, therefore, to provide in a vinegar fermentation system of the above described type a comparatively simple control arrangement for enabling the process to be run in an optimum fashion.

The present invention enables this objective to be achieved by virtue of the fact that the control arrangement is connected with a volume flowmeter for measuring the quantity of alcohol fed into the main fermentation tank and with a device for sensing an upper and a lower liquid level in the main fermentation tank. The arrangement is such that, on the one hand, once the addition of a predetermined quantity of alcohol is indicated by the associated volume flowmeter as having been attained, the activation of the alcohol feed pump is blocked and the connecting line between the two fermentation tanks is opened, and that, on the other hand, when the lower liquid level has been reached in the main fermentation tank as indicated by the liquid level sensing device, the connecting line is closed and the feed pump for the mash is activated until the upper liquid level has again been reached. At that point, the control arrangement again permits the activation of the alcohol feed pump. Thus, the control arrangement according to the present invention ensures that the discharge of finished vinegar from the secondary fermentation tank is controllable in dependence on the alcohol concentration in that tank.

Since the alcohol feed pump connected with the main fermentation tank is activated by the control arrangement when the alcohol concentration drops below a predetermined desired value, the alcohol feed is first delayed until the starting concentration of the alcohol in the mash has sunk by virtue of the vinegar fermentation to the predetermined desired value. Thereafter the alcohol concentration is maintained constant in an advantageous fashion because the pump feeds in only such a quantity of alcohol as is required to compensate for the alcohol consumption and to maintain the alcohol concentration at the desired value thereof. This controlled addition of alcohol is interrupted when the total quantity of the added alcohol has reached a predetermined value as indicated by the volume flowmeter.

Through this limiting of the total quantity of added alcohol, the highest total concentration is fixed, concurrently with which, by virtue of the fact that the alcohol concentration is maintained constant, it is ensured that the acetic acid content cannot rise above a desired amount. The indication by the volume flowmeter that the predetermined total quantity of alcohol has been fed into the main fermentation tank can thus be viewed as a control signal for the ending of a fermentation period in the main fermentation tank. The control arrangement then causes the connecting line between the main fermentation tank and the secondary fermentation tank to be opened in order to feed a portion of the substrate from the main tank into the secondary tank. The discharge of this partial quantity of the substrate is terminated when the lower liquid level in the main fermentation tank is reached as sensed by the level sensing device provided for that purpose. The control arrangement, in response to the signal from the liquid level sensing device, then causes the connecting line between the two fermentation tanks to be closed and the feed pump for the mash to be activated, until the level sensing device indicates the attainment of the upper liquid level in the main fermentation tank. In response to the resultant control signal, the feed pump for the mash is deactivated and the activation of the feed pump for the alcohol is again permitted, so that after the starting of the new fermentation period and the concomitant sinking of the alcohol content to the desired concentration thereof, fresh alcohol can be again added to maintain the alcohol concentration constant.

The continued fermentation of the transferred substrate in the secondary fermentation tank takes place with an increase of the acetic acid concentration to above 15 g/100 ml, until the alcohol concentration has sunk to a predetermined lower limit value. The discharge of the finished vinegar from the secondary fermentation tank then can be effected under the control of either a device for analyzing the alcohol concentration or a device for monitoring the generation of heat in that tank.

For the purpose of ending the discharge of vinegar from the secondary fermentation tank, there can be provided a device for sensing the attainment of a lower liquid level in this tank, which device, when the lower liquid level has been reached, sends a signal to a control device for terminating the vinegar discharge. When the predetermined lower liquid level in the secondary fermentation tank is reached, furthermore, the aerator for the secondary fermentation tank can also be deactivated by the associated control device until fresh substrate is to be transferred from the main fermentation tank into the secondary fermentation tank, because during this time interval aeration of the liquid in the latter tank is not required.

In order to avoid, during the transfer of fresh substrate from the main fermentation tank into the secondary fermentation tank, a sudden leap in the alcohol and acetic acid concentration values, the existing acetic acid and alcohol concentrations in the secondary fermentation tank can be adapted to the corresponding concentration values of the incoming substrate by a mixing thereof with fresh mash. Since these concentration values are determined by the fermentation process in progress in the main fermentation tank, it is sufficient for this purpose to feed into the secondary fermentation tank a predetermined quantity of mash having prescribed alcohol and acetic acid concentrations. A simple control of this addition of mash is rendered possible by setting the liquid level sensing device associated with the secondary fermentation tank to respond, apart from the previously mentioned lower liquid level, to an intermediate liquid level between that lower level and an upper level, with the arrangement being such that the said control device responding to this liquid level sensing device will activate a mash feed pump connected with the secondary fermentation tank when the lower liquid level is reached and will continue such activation until the intermediate liquid level has been sensed by the level sensing device.

In the event that, at the time the substrate is discharged from the main fermentation tank, the fermentation in the secondary tank has for any reason not yet been completed, then the addition of the substrate into the secondary fermentation tank should be held in abeyance. This can be achieved very simply by causing the liquid level sensing device associated with the secondary fermentation tank to send a signal to the control device associated with the connecting line between the two fermentation tanks so as to activate that control device in the sense of blocking the connecting line when an indication is received that the aforesaid intermediate liquid level has been exceeded. The location of the liquid level in the secondary fermentation tank above the predetermined intermediate liquid level indicates that the discharge of vinegar from the secondary fermentation tank has either not yet been performed or has not yet been completed. The blocking of the connecting line in dependence on the existence of a liquid level in the secondary fermentation tank which is above the specified intermediate liquid level thus affords the desired assurance against an inadvisable premature transfer of substrate into the secondary fermentation tank.

The blocking of the connecting line between the two fermentation tanks in response to the liquid level existing in the secondary fermentation tank should, of course, be so controlled as to have no adverse effect on the regular feed of substrate into the secondary tank, because otherwise upon the liquid reaching a level in that tank above the intermediate liquid level the feed would be interrupted. For this purpose, whenever the connecting line is opened at a liquid level in the secondary fermentation tank being lower than the liquid level that would cause the blocking of the connecting line, the associated control device can be set to activate a timing device for delaying the blocking of the connecting line until the regular filling of the secondary fermentation tank has been achieved. The reason for the provision of this aspect of the control arrangement according to the present invention is that the feed of the substrate from the main fermentation tank into the secondary fermentation tank requires a predetermined time interval during which the connecting line between the two tanks is, of course, always held open.

BRIEF DESCRIPTION OF THE DRAWING

The foregoing and other objectives, characteristics and advantages of the present invention will be more clearly understood from the following detailed description of a preferred embodiment thereof when read in conjunction with the accompanying drawing, in which:

The sole figure illustrates schematically an arrangement according to the present invention for controlling a two-stage submerged vinegar fermentation process.

DESCRIPTION OF THE PREFERRED EMBODIMENT

Referring now to the drawing in greater detail, it will be seen that the illustrated vinegar fermentation system basically includes a main fermentation tank 1 and a secondary fermentation tank 2, the latter being connected with the former via a connecting line 3. The main fermentation tank 1 is connected with a mash supply tank 4 on the one hand and with an alcohol supply tank 5 on the other via respective feed lines 8 and 9 having incorporated therein respective feed pumps 6 and 7. The discharge ends 8a and 9a of the feed lines 8 and 9 are located within the tank 1 near the bottom thereof adjacent the discharge end 10a of an air aspirating line 10, with all three discharge ends being arranged, in a manner well known per se and hence not illustrated in detail, in the vicinity of the rotor (not shown) of an aerator 11 arranged in the bottom region of the main fermentation tank 1 in order to ensure a uniform and intimate mixing of all added mash and alcohol with the fermenting liquid already in the tank while the entire mixture is being subjected to simultaneous aeration. The rates of flow of the mash, alcohol and air through their respective feed lines 8, 9 and 10 into the main fermentation tank 1 can be regulated by respective throttle valves 12, 12' and 12" and monitored by respective flowmeters 13, 13' and 13". The feed lines 8 and 9 are further equipped, in their regions connected to the mash and alcohol supply tanks 4 and 5, with respective shut-off valves 14 and 14', and the air aspirating line 10 is in usual manner equipped with an air filter 15.

For the control of the feed of alcohol and mash into the tank 1 there is provided in accordance with the present invention a control arrangement by which the feed pumps 6 and 7 can be switched on and off, i.e., activated and deactivated, independently of one another, on the one hand in dependence on the level of the liquid contents of the main fermentation tank and on the other hand in dependence on the alcohol concentration of the liquid contents of that tank. To this end, the control arrangement includes a first control device 16 of any suitable type, for example, a controller including an appropriately programmed microprocessor, which is connected via electrical output signal lines 16a and 16b to the respective operating control elements 6a and 7a of the pumps 6 and 7. The control arrangement further includes a bi-level liquid level sensing device 17 mounted on the main fermentation tank 1 and having a float-type sensor 17a and a pair of signal-generating elements 17b and 17c positioned, respectively, to respond to the liquid in the tank reaching an upper level 18 or a lower level 19 and adapted to transmit appropriate electrical signals to the controller 16 via input signal lines 16c and 16d. It will be understood, of course, that although the sensing device 17 in the illustrated embodiment of the invention is shown as being equipped with a float-type sensor, other types of sensing devices (optical, capacitive, etc.) could be used. The control arrangement still further includes an alcohol analyzer 20 of any suitable type, for example, an apparatus such as is described in U.S. Pat. No. 3,290,294, which is also mounted on the main fermentation tank and is electrically connected via an input signal line 16e to the control device 16, a volume flowmeter 21 which is incorporated in the alcohol feed line 9 and is electrically connected via an input signal line 16f to the control device 16, and a shut-off valve 22 and a feed pump 23 which are incorporated in the connecting line 3 between the two fermentation tanks and the operating control elements 22a and 23a of which are connected with respective output signal lines 16g and 16h from the control device 16.

It will be understood from the description so far, that when the alcohol concentration in the main fermentation tank 1 sensed by the analyzer 20 drops below a predetermined value, the feed pump 7 is activated by the control device 16. Alcohol is then fed into the main fermentation tank until the predetermined desired value of the alcohol concentration has been reachieved and a corresponding signal is sent to the control device 16 by the analyzer 20. As a result, after the starting portion of a fermentation period and the associated sinking of the alcohol concentration to the desired value thereof, the alcohol concentration is maintained constant, which has a beneficial effect on the vinegar fermentation. The quantities of alcohol fed into the main fermentation tank 1 from the alcohol supply tank 5 are sensed by the flowmeter 21 in the feed line 9, which instrument, when a predetermined total quantity of alcohol has been fed into the tank, transmits a signal via the line 16f to the control device 16 to cause the latter in turn to transmit a signal via the line 16b to the alcohol feed pump 7 tending to deactivate the same.

Since by virtue of the described progress of the process at constant alcohol concentration, the acetic acid concentration increases in the same extent as the total concentration and the increase in the total concentration is determined by the fed in quantity of alcohol, the attainable acetic acid concentration in the main fermentation tank 1 can, by a limiting of the admitted quantity of alcohol, also be limited to a value at most as high as 15 g/100 ml. This restriction of the acetic acid concentration in the main fermentation tank is essential in order to maintain the multiplication capacity of the vinegar bacteria for the duration of a plurality of successive fermentation periods.

When the flowmeter 21 shows that the desired total quantity of alcohol has been fed into the main fermentation tank, the then current fermentation period in the main fermentation tank is terminated. Upon transmission of the resultant signal to the control device 16 via the line 16f, a portion of the contents of the main fermentation tank 1 is discharged and transferred into the secondary fermentation tank 2 via the connecting line 3. For this purpose, the control device 16 operates on the one hand to open the valve 22 by a signal transmitted to the operating control element 22a thereof via the line 16g and on the other hand to start the feed pump 23 by a signal transmitted to the operating control element 23a thereof via the line 16h, thereby to cause the substrate to be fed from the main fermentation tank 1 into the secondary fermentation tank 2. As in the case of the feed lines 8, 9 and 10 in the main fermentation tank, the discharge end 3a of the transfer feed line 3 is located in the bottom region of the secondary fermentation tank in the vicinity of the rotor (not shown) of a submerged aerator 24 and adjacent the discharge end 25a of an associated air aspirating line 25 which is equipped with a filter 26, a throttle valve 27 and a flowmeter 28, so that the substrate entering the tank 2 is uniformly and intimately admixed and aerated with the liquid remaining in that tank from the preceding process stage.

The discharge of substrate from the main fermentation tank 1 into the secondary fermentation tank 2 is terminated when the liquid in the main fermentation tank reaches the lower level 19, at which time the liquid level sensing device 17 transmits an appropriate signal via the line 16d to the control device 16 which causes the latter to close the valve 22 and to deactivate the pump 23. At that point a new fermentation period is commenced in the main fermentation tank by an injection of fresh mash from the supply tank 4, with the feed pump 6 being activated for this purpose by the control device 16 via the line 16a until the level sensing device 17 indicates that the liquid in the main fermentation tank has again reached the upper level 18. The described process is then repeated when the alcohol concentration has again dropped below the aforesaid predetermined value thereof.

The substrate transferred into the secondary fermentation tank 2 is aerated by means of the aerator 24 in order to oxidize the still remaining alcohol, up to a residual alcohol content of, for example, 0.2 vol. %, to acetic acid. During this phase, the acetic acid concentration rises above 15 g/100 ml and in particular without multiplication of the vinegar bacteria. The quantity of air aspirated into the tank through the filter 26 can be adjusted with the aid of the throttle valve 27.

Referring now to the secondary fermentation tank 2, mounted on the same are an alcohol analyzer 29 (of essentially the same type as the alcohol analyzer 20) which is electrically connected with a second control device 30 (of essentially the same type as the first control device 16) via an input signal line 30a, and a liquid level sensing device 35 having a float-type sensor 35a and three signal-generating elements 35b, 35c and 35d positioned, respectively, to respond to the liquid in the tank reaching a lower level 34, an intermediate level 40 between the lower level and an upper level 41, and a level 42 somewhat higher than the intermediate level 40. Of these signal-generating elements, the elements 35b and 35c are adapted to transmit appropriate electrical input signals to the control device 30 via lines 30b and 30c, while the element 35d is adapted to transmit an input signal to the first control device 16 via a line 16i. A vinegar discharge line 32 having incorporated therein a feed pump 31 and a shut-off valve 33 communicates at its intake end 32a with the bottom region of the tank 2 and at its discharge end (not shown) with a receiver (not shown) for the discharged vinegar, the control device 30 having respective output signal lines 30d and 30e connected, respectively, to the operating control element 31a of the vinegar feed pump 31 and the operating control element 24a of the aerator 24. A further output signal line 16j runs from the control device 16 to the control device 30. Downstream of the feed pump 31 the discharge line 32 preferably communicates with a branch discharge line 32' having incorporated therein a shut-off valve 33' and leading to a second receiver (not shown) for discharged vinegar.

Insofar as the second stage of the fermentation process is concerned, the lowering of the alcohol concentration in the secondary fermentation tank 2 is monitored by the analyzer 29, and the control arrangement here ensures that when the alcohol concentration reaches a prescribed lower limit value, the control device 30 activates the discharge feed pump 31 in the line 32, thereby to enable finished vinegar to be transferred to a receiver, either through the line 32 or the line 32' depending on which of the valves 33 and 33' is open. The discharge feed pump 31 is deactivated and the vinegar discharge terminated when the liquid in the secondary fermentation tank reaches the lower level 34 and the sensing device 35 transmits the requisite signal via the line 30b to the control device 30.

The process could now be continued through the transfer of a fresh quantity of substrate from the main fermentation tank 1 into the secondary fermentation tank 2. In accordance with the illustrated embodiment of the invention, however, prior to such a transfer, mash from a supply tank 36 is fed into the secondary fermentation tank through a feed line 37 having incorporated therein a shut-off valve 38, a feed pump 39 having its operating control element 39a connected to the control device 30 by an output signal line 30f of the latter, a throttle valve 47 and a flowmeter 48. The discharge end 37a of the feed line 37 is located in the bottom region of the tank 2 adjacent the discharge ends 3a and 25a of the lines 3 and 25. When the level sensing device 35 emits the signal that the lower level 34 has been reached, the control device 30 activates the mash feed pump 39 via the line 30f to cause fresh mash to be fed into the secondary fermentation tank 2, with this introduction of mash, the rate of which can be adjusted by means of the throttle valve 47 and monitored by the flowmeter 48, being terminated when the liquid in the tank 2 rises to the level 40 intermediate the lower level 34 and the upper level 41. The signal generated by the sensing device 35 when the intermediate level 40 has been reached causes the control device 30 to deactivate the feed pump 39. It can be seen, therefore, that with the aid of such an injection of mash, the contents of the secondary fermentation tank 2 can be adjusted, prior to the injection of fresh substrate from the main fermentation tank 1, to have alcohol and acetic acid concentration values the same as those existing in the substrate, in order to create for the secondary fermentation stage especially favorable and advantageous conditions.

When, in the main fermentation tank 1, a fermentation period has ended before the discharge of vinegar from the secondary fermentation tank 2 has been performed, then the injection of substrate from the main tank into the secondary tank must be delayed. From the standpoint of control technology, this temporary blocking of the discharge of substrate from the main fermentation tank can be effected quite simply if the sensing device 35 in the secondary fermentation tank 2 is constructed to respond to the liquid in that tank being at a level 42 somewhat above the intermediate level 40. Thus, when the liquid is indicated as being at the level 42, which represents the condition of more than a permissible minimum amount of vinegar still being in the secondary fermentation tank, the control device 16 receives a signal from the sensing device 35 via the line 16$i$ and applies an output signal via the line 16$g$ to the valve 22 and causes it to be shifted in a sense tending to block the connecting or transfer feed line 3. By virtue of this control action, the shut-off valve 22 cannot be opened and the pump 23 cannot be activated.

Such a blocking of the connecting line 3 should, understandably, not interfere in any way with the regular feed of substrate from the main fermentation tank 1 into the secondary fermentation tank 2, because otherwise the latter could not be filled to the upper level 41. It is for this reason that the blocking of the connecting line 3 must be inhibited whenever the regular feed of substrate into the secondary fermentation tank 2 is to be made. That is accomplished with the aid of a timing device 43, which is connected with the control device 16 via output and input signal lines 16$k$ and 16$m$ so that it will be energized when the connecting line 3 is open upon the liquid in the secondary fermentation tank 2 being below the level 42. The timing device provides a running time interval at least corresponding to the duration of the injection of the substrate into the secondary fermentation tank and ensures that the control device 16 generates signals tending to inhibit the blocking of the connecting line 3.

In the event substrate is to be pumped from the main fermentation tank 1 into a different receiver than the secondary fermentation tank 2, this can be effected through a branch line 3' which is connected with the connecting line 3 downstream of the pump 23. For the purpose of an alternating opening and closing of the connecting line 3 and the branch line 3', the two lines are equipped with respective shut-off valves 44 and 44'.

Inasmuch as at a high total concentration accompanied by a rising acetic acid concentration, a lower fermentation temperature is more favorable for the vinegar bacteria, the cooling of both the main fermentation tank 1 and the secondary fermentation 2 can be controlled through an appropriate activation of, i.e., flow of coolant through, respective cooling coils 45 and 45' associated with the two tanks.

It should be pointed out that aeration of the residual contents of the secondary fermentation tank 2 after the extraction of vinegar therefrom is actually not necessary. The aeration must, however, be restarted when fresh substrate is injected from the main fermentation tank 1. Thus, the signal emitted by the analyzer 29 when the alcohol concentration in the secondary fermentation tank sinks to a lower limiting value, which causes the control device 30 to activate the discharge feed pump 31 for commencing the vinegar discharge operation, can also serve to trigger the control device 30 to emit a signal via the line 30$e$ to deactivate the aerator 24. Thereafter, when the discharge of vinegar is completed, the emission of a signal by the control device 16 via the lines 16$g$ and 16$h$ to open the connecting line 3 between the two tanks for the transfer of fresh substrate is necessarily accompanied by the transmission of a signal from the control device 16 via the line 16$j$ to the control device 30 to cause the latter to reactivate the aerator 24.

Although in the illustrated embodiment of the present invention, the alcohol concentration in the secondary fermentation tank 2 is monitored with the aid of an analyzer 29, the provision of such an analyzer for the secondary fermentation tank is not indispensable. Since the generation of heat stops with the termination of the fermentation process, it would be just as possible, by way of example, to control the discharge of the finished vinegar from the secondary fermentation tank through a monitoring of the heat generated therein.

By way of summary, therefore, it can be seen that the present invention provides a control arrangement for a two-stage submerged vinegar fermentation system. Generally speaking, the system includes a main fermentation tank and a secondary fermentation tank equipped with first and second aeration means, respectively, a first feed line and a second feed line connected to the main fermentation tank for establishing communication between that tank and a supply of mash and a supply of alcohol, respectively, a first feed pump and a second feed pump incorporated in the first and second feed lines, respectively, for charging mash and alcohol into the main fermentation tank, a third feed line connected to the secondary fermentation tank for establishing communication between the same and receiving means for finished vinegar, a third feed pump incorporated in the third feed line for discharging vinegar from the secondary fermentation tank, a fourth feed line connected to and establishing communication between the main fermentation tank and the secondary fermentation tank, and a selectively openable and closable shut-off valve incorporated in the fourth feed line for permitting or blocking the transfer of partially fermented substrate therethrough from the main to the secondary fermentation tank, and wherein the control arrangement includes first analyzer means connected with the main fermentation tank for sensing the alcohol concentration in the liquid in that tank, and first controller means associated with the main fermentation tank, the first controller means being responsive to signals emitted by the first analyzer means and operatively connected with the second feed pump for activating the latter in dependence on the difference between the existing alcohol concentration of the liquid in the main fermentation tank as sensed by the first analyzer means and a preset desired value for an upper limit of the alcohol concentration.

Within this environment, the improvement in the control arrangement provided by the present invention comprises the following features:

(a) a volume flowmeter is incorporated in the second feed line for measuring the quantity of alcohol charged into the main fermentation tank;

(b) first liquid level sensing means are associated with the main fermentation tank and are operable for sensing the attainment by the liquid in the latter of a predetermined upper level and a predetermined lower level, respectively;

(c) a fourth feed pump is incorporated in the fourth feed line for transferring therethrough and into the secondary fermentation tank partially fermented substrate discharged from the main fermentation tank;

(d) the first controller means are further responsive to signals emitted by the volume flowmeter and the first liquid level sensing means and are further operatively connected with the shut-off valve and the fourth feed pump, (i) for blocking the activation of the second feed pump, opening the shut-off valve and activating the fourth feed pump upon a predetermined quantity of alcohol having been charged into the main fermentation tank as measured by the volume flowmeter, and (ii) for closing the shut-off valve and deactivating the fourth feed pump upon the liquid in the main fermentation tank having sunk to the lower level as sensed by the first liquid level sensing means, for concomitantly activating the first feed pump until sufficient mash has been charged into the main fermentation tank to raise the liquid in the latter to the upper level as sensed by the first liquid level sensing means, and for thereafter deactivating the first feed pump and again permitting the activation of the second feed pump;

(e) second analyzer means are connected with the secondary fermentation tank for sensing the alcohol concentration in the liquid in the secondary fermentation tank; and (f) second controller means are associated with the secondary fermentation tank, the second controller means being responsive to signals emitted by the second analyzer means and operatively connected to the third feed pump for activating the same upon the alcohol concentration of the liquid in the second fermentation tank having sunk to a predetermined value.

It will be understood that the foregoing description of a preferred embodiment of the control arrangement according to the present invention is for purposes of illustration only and that the herein disclosed control arrangement and its manner of operation are susceptible to a number of changes and modifications none of which entails any departure from the spirit and scope of the present invention as defined by the hereto appended claims.

What is claimed is:

1. In a control arrangement for a two-stage submerged vinegar fermentation system, (A) wherein said system includes a main fermentation tank and a secondary fermentation tank equipped with first and second aeration means, respectively, a first feed line and a second feed line connected to said main fermentation tank for establishing communication between said main fermentation tank and a supply of mash and a supply of alcohol, respectively, a first feed pump and a second feed pump incorporated in said first and second feed lines, respectively, for charging mash and alcohol into said main fermentation tank, a third feed line connected to said secondary fermentation tank for establishing communication between said secondary fermentation tank and receiving means for finished vinegar, a third feed pump incorporated in said third feed line for discharging vinegar from said secondary fermentation tank, a fourth feed line connected to and establishing communication between said main fermentation tank and said secondary fermentation tank, and a selectively openable and closable shut-off valve incorporated in said fourth feed line for permitting or blocking the transfer of partially fermented substrate therethrough from said main fermentation tank to said secondary fermentation tank, and (B) wherein said control arrangement includes first analyzer means connected with said main fermentation tank for sensing the alcohol concentration of the liquid in said main fermentation tank, and first controller means associated with said main fermentation tank, said first controller means being responsive to signals emitted by said first analyzer means and operatively connected with said second feed pump for activating the latter in dependence on the difference between the existing alcohol concentration of the liquid in said main fermentation tank as sensed by said first analyzer means and a preset desired value for an upper limit of the alcohol concentration;

the improvement comprising that:

a) a volume flowmeter is incorporated in said second feed line for measuring the quantity of alcohol charged into said main fermentation tank;

(b) first liquid level sensing means are associated with said main fermentation tank and are operable for sensing the attainment by the liquid in the latter of a predetermined upper level and a predetermined lower level, respectively;

(c) a fourth feed pump is incorporated in said fourth feed line for transferring therethrough and into said secondary fermentation tank partially fermented substrate discharged from said main fermentation tank;

(d) said first controller means are further responsive to signals emitted by said volume flowmeter and said first liquid level sensing means and are further operatively connected with said shut-off valve and said fourth feed pump, (i) for blocking the activation of said second feed pump, opening said shut-off valve and activating said fourth feed pump upon a predetermined quantity of alcohol having been charged into said main fermentation tank as measured by said volume flowmeter, and (ii) for closing said shut-off valve and deactivating said fourth feed pump upon the liquid in said main fermentation tank having sunk to said lower level as sensed by said first liquid level sensing means, for concomitantly activating said first feed pump until sufficient mash has been charged into said main fermentation tank to raise the liquid in the latter to said upper level as sensed by said first liquid level sensing means, and for thereafter deactivating said first feed pump and again permitting the activation of said second feed pump;

(e) second analyzer means are connected with said secondary fermentation tank for sensing the alcohol concentration of the liquid in said secondary fermentation tank; and (f) second controller means are associated with said secondary fermentation tank, said second controller means being responsive to signals emitted by said second analyzer means and operatively connected to said third feed pump for activating the same upon the alcohol concentration of the liquid in said secondary fermentation tank having sunk to a predetermined value.

2. In a control arrangement as claimed in claim 1; the further improvement comprising that:
   (g) second liquid level sensing means are associated with said secondary fermentation tank for sensing the attainment by the liquid in the latter of a predetermined lowest level; and
   (h) said second controller means are responsive to signals emitted by said second liquid level sensing means for deactivating said third feed pump upon the liquid in said secondary fermentation tank having sunk to said lowest level therein for terminating the discharge of finished vinegar from said secondary fermentation tank.

3. In a control arrangement as claimed in claim 2; the further improvement comprising that:
   (j) said second liquid level sensing means are operable for sensing the attainment by the liquid in said secondary fermentation tank of a level intermediate said lowest level and a highest level;
   (k) a fifth feed line is connected to said secondary fermentation tank for establishing communication between said secondary fermentation tank and a supply of mash, and a fifth feed pump is incorporated in said fifth feed line for charging mash into said secondary fermentation tank;
   (m) said second controller means are responsive to signals emitted by said second liquid level sensing means upon attainment by the liquid in said secondary fermentation tank of said intermediate level and are operatively connected with said fifth feed pump for activating the latter upon the liquid in said secondary fermentation tank having sunk to said lowest level and for deactivating said fifth feed pump upon the liquid in said secondary fermentation tank having risen to said intermediate level.

4. In a control arrangement as claimed in claim 3; the further improvement comprising that:
   (n) said second liquid sensing means are further operable for sensing the attainment by the liquid in said secondary fermentation tank of an additional level somewhat above said intermediate level but below said highest level; and
   (o) said first controller means are responsive to signals emitted by said second liquid level sensing means upon the liquid in said secondary fermentation tank being at least as high as said additional level and are operable to control said shut-off valve and said fourth feed pump in said fourth feed line in the sense of blocking the same.

5. In a control arrangement as claimed in claim 4; the further improvement comprising that:
   (p) timing means are associated with said first controller means, said timing means being responsive to signals emitted by said first controller means and operatively connected with the latter for counteracting, as long as the liquid in said secondary fermentation tank is below said additional level, any signal output of said first controller means the effect of which would be an operation of said shut-off valve and said fourth feed pump in said fourth feed line in the sense of blocking the latter.

6. In a control arrangement as claimed in claim 2; the further improvement comprising that:
   (q) said second controller means are operatively connected with said second aeration means for deactivating the latter upon the liquid in said secondary fermentation tank having sunk to said lowest level therein as sensed by said second liquid level sensing means.

7. In a control arrangement as claimed in claim 6; the further improvement comprising that:
   (r) said second controller means are responsive to said first controller means and are operable, upon receiving from the latter a signal concomitant with the opening of said shut-off valve and the activation of said fourth feed pump, to reactivate said second aeration means.

* * * * *